US008496707B2

(12) United States Patent
Adamo

(10) Patent No.: US 8,496,707 B2
(45) Date of Patent: Jul. 30, 2013

(54) INTERVERTEBRAL DISC PROSTHESIS FOR THE CERVICAL SPINE IN THE DOG

(76) Inventor: Pietro Filippo Adamo, San Mateo, CA (US)

( * ) Notice: Subject to any disclaimer, the term of this patent is extended or adjusted under 35 U.S.C. 154(b) by 329 days.

(21) Appl. No.: 12/015,025

(22) Filed: Jan. 16, 2008

(65) Prior Publication Data

US 2008/0306597 A1 Dec. 11, 2008

Related U.S. Application Data

(60) Provisional application No. 60/881,344, filed on Jan. 19, 2007.

(51) Int. Cl.
*A61F 2/44* (2006.01)
(52) U.S. Cl.
USPC .............. 623/17.14; 623/17.11; 623/17.15; 623/17.16
(58) Field of Classification Search
USPC .............................. 623/17.11–17.16; 606/257
IPC ................................. A61F 2/44; A61B 17/70
See application file for complete search history.

(56) References Cited

U.S. PATENT DOCUMENTS

| | | | | |
|---|---|---|---|---|
| 5,314,477 A * | 5/1994 | Marnay | | 623/17.15 |
| 5,562,738 A * | 10/1996 | Boyd et al. | | 623/17.15 |
| 6,610,093 B1 * | 8/2003 | Pisharodi | | 623/17.15 |
| 6,764,515 B2 * | 7/2004 | Ralph et al. | | 623/17.13 |
| 6,989,032 B2 * | 1/2006 | Errico et al. | | 623/17.14 |
| 7,014,658 B2 * | 3/2006 | Ralph et al. | | 623/17.13 |
| 7,083,651 B2 * | 8/2006 | Diaz et al. | | 623/17.13 |
| 7,214,244 B2 * | 5/2007 | Zubok et al. | | 623/17.14 |
| 7,276,082 B2 * | 10/2007 | Zdeblick et al. | | 623/17.15 |
| 2003/0135278 A1 * | 7/2003 | Eckman | | 623/17.14 |
| 2003/0187506 A1 * | 10/2003 | Ross et al. | | 623/17.13 |
| 2003/0204261 A1 * | 10/2003 | Eisermann et al. | | 623/17.14 |
| 2003/0208273 A1 * | 11/2003 | Eisermann et al. | | 623/17.14 |
| 2003/0233146 A1 * | 12/2003 | Grinberg et al. | | 623/17.14 |
| 2005/0060035 A1 * | 3/2005 | Errico et al. | | 623/17.15 |
| 2005/0228500 A1 * | 10/2005 | Kim et al. | | 623/17.13 |
| 2007/0050033 A1 * | 3/2007 | Reo et al. | | 623/17.12 |
| 2007/0191860 A1 * | 8/2007 | Heinz et al. | | 606/99 |

OTHER PUBLICATIONS

Adamo et al., "In Vitro Biomechanical Comparison of Cervical Disk Arthroplasty, Ventral Slot Procedure, and Smooth Pins with Polymethylmethacrylate Fixation at Treated and Adjacent Canine Cervical Motion Units," *Vet. Surgery*, 36:729-741 (2007).

(Continued)

*Primary Examiner* — Eduardo C Robert
*Assistant Examiner* — Julianna N Harvey
(74) *Attorney, Agent, or Firm* — Patent Jurist; Georgiy L. Khayet

(57) ABSTRACT

A cervical disc prosthesis or intervertebral disc prosthesis that includes a first disc comprising a protrusion connected to a disc body and a convex surface facing a first cervical vertebra when implanted, and a second disc comprising a socket recessed in a disc body, and a convex surface facing a second cervical vertebra when implanted. The second disc remains substantially parallel to the first disc and axially spaced from the first disc. The protrusion is adapted to fit into the socket to join the first disc with the second disc, and the protrusion is fit for pivoting movement into the socket. Also provided is a method for implanting the inventive cervical disc prosthesis or the inventive intervertebral disc prosthesis into an intervertebral disc area defined between two adjacent vertebrae.

21 Claims, 9 Drawing Sheets

OTHER PUBLICATIONS

Koehler et al., "Effect of a ventral sloth procedure and of smooth or positive-profile threaded pins with polymethylmethacrylate fixation on intervertebral biomechanics at treated and adjacent canine cervical vertebral motion units," *Am. J. Vet. Res.*, 66:678-687 (2005).

Kunz et al., "A Multi-Degree of Freedom System for Biomechanical Testing," *J. Biomech. Eng.*, 116(3):371-373 (1994).

* cited by examiner

INTERVERTEBRAL DISC PROSTHESIS FOR THE CERVICAL SPINE IN THE DOG

CROSS-REFERENCE TO RELATED APPLICATIONS

This invention claims priority to U.S. Provisional Patent Application Ser. No. 60/881,344, filed Jan. 19, 2007.

FIELD OF THE INVENTION

This invention is related to the field of intervertebral prosthetic devices and methods.

BACKGROUND OF THE INVENTION

Disc-associated caudal cervical spondylomyelopathy (CCSM) is a common disease in dogs. It is especially prevalent among large dogs such as the Doberman, Rottweiler, Dalmatian, Greyhound, and Labrador breeds. The hallmark of the illness is degeneration of one or multiple cervical (neck) discs, with the associated thickening of the ligaments that hold the vertebrae together. The bulging from the degenerated disc and the thickened ligaments may cause significant spinal cord compression and vertebral instability, which may be exacerbated by neck movements. This condition is best known as "wobbler syndrome" or "disc-associated wobbler syndrome", causing the dogs to literally wobble and lose balance. If left untreated, the illness eventually causes paralysis.

The current standard of care for animals with the CCSM syndrome is to surgically remove the bulging disc and the thickened ligaments by a surgical procedure called "ventral slot", and thus eliminate the source of compression in the spine. However, this method does not improve the instability, and often the newly created space between the vertebrae further collapses. Another known surgical treatment is the ventral slot technique associated with "distraction and fusion". In addition to spinal decompression, this technique maintains the intervertebral space distant, providing immobility of the two affected vertebrae. However, both surgical techniques change drastically the spinal biomechanics and up to one-third of dogs treated in this manner experience symptoms again in another area of the spine; this is called "domino effect", "domino lesion", or "adjacent segment disease". Recurrence can be caused by compression at the original site, by a domino lesion at an adjacent site, or a combination of both. Recurrence frequently occurs between 6 months and 4 years after the original surgery, and usually around 2 years after surgery. Accordingly, it would be beneficial to provide a device for alleviating the pain and for the treatment of disc-associated diseases in dogs and other mammals.

BRIEF SUMMARY

This invention provides a cervical disc prosthesis that includes a first disc comprising a first disc body with top and bottom surfaces, where the top surface has a protrusion, and where the bottom surface is convex, and a second disc comprising a second disc body with top and bottom surfaces, where the bottom surface is convex, and where the top surface has a socket recessed therein. The protrusion of the first disc is sized and shaped to pivot in the socket of the second disc, and the first and second discs remain substantially parallel to and axially spaced from each other with their top surfaces facing each other.

The first disc may be a caudal disc and the second disc may be a cranial disc. Alternatively, the first disc may be a cranial disc and the second disc may be a caudal disc. The discs of the prosthesis are preferably made of stainless steel or titanium alloy.

This invention provides intervertebral disc prosthesis for placement between two adjacent cervical vertebrae. The prosthesis includes a first end member for contacting the first vertebra when implanted, and a second end member for contacting the second vertebra when implanted. The first end member has a central axis and has a concave surface with a central axis. The first end member also has a convex surface facing a first cervical vertebra when implanted. The second end member has a central axis and has a first convex surface with a central axis. The first convex surface faces the first end member. The second end member also has a second convex surface facing a second cervical vertebra when implanted. The concave surface of the first end member coaptates with the first convex surface of the second end member to provide approximately thirty degrees of freedom.

The first end member may be a caudal disc and the second end member may be a cranial disc. Alternatively, the first end member may be a cranial disc and the second end member may be a caudal disc. The end members of the prosthesis are preferably made of stainless steel or titanium alloy.

The cross-section of the inventive cervical disc or the inventive intervertebral disc prosthesis may be approximately rectangular. As well, at least one convex surface facing at least one cervical vertebra may include a groove.

The axes of the prosthesis are coaxial. The prosthesis may include at least one removable fin that is attached to at least one of the discs. The prosthesis may be sized to fit between two cervical vertebrae in a dog.

This invention provides a method for implanting the inventive cervical disc prosthesis or the inventive intervertebral disc prosthesis into an intervertebral disc area defined between adjacent cervical vertebrae. Introduction of the cervical disc prosthesis may be performed using cervical arthroplasty.

DETAILED DESCRIPTION OF THE DRAWINGS AND THE PRESENTLY PREFERRED EMBODIMENTS

Figure 1:
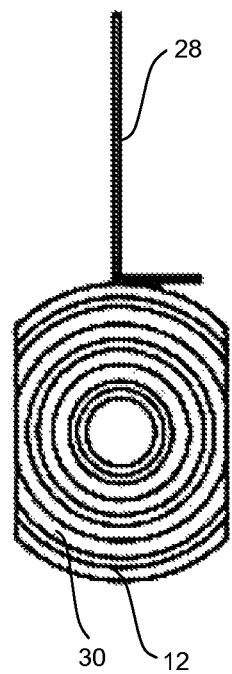
FIG. 1 is a top plan view of a first disc of the prosthetic device taken through line 1-1 in FIG. 2.

For the purpose of promoting an understanding of the principles of the invention, reference will now be made to certain preferred embodiments thereof and specific language will be used to describe the same. It will nevertheless be understood that no limitation of the scope of the invention is thereby intended. Any alterations, further modifications and applications of the principles of the invention as described herein are being contemplated as would normally occur to one skilled in the art to which the invention relates.

Unless defined otherwise, all technical and scientific terms used herein have the same meaning as commonly understood to one of ordinary skill in the art to which this invention belongs. In order to provide a clear and consistent understanding of the specification and the claims, the following definitions are provided.

The terms "a", "an", "the" and the like, unless otherwise indicated, include plural forms.

The terms "subject" or "recipient" as used in this application refer to mammals. These terms especially refer to non-human animals, and especially to dogs.

The term "cranial" as used in this application means of or relating to the skull. A cranial disc is a disc that is directed toward or situated near the skull of the subject.

The term "caudal" as used in this application means of or relating to a tail. A caudal disc is a disc that is directed toward or situated near the tail or posterior part of a subject's body.

The term "coaxial" means that two or more forms share a common axis. Coaxial is the three-dimensional linear analog of "concentric".

The terms "treating" or "treatment" as used in this application refer to the treating or treatment of a disease or medical condition. Examples of a disease or a medical condition are disc-associated caudal cervical spondylomyelopathy (CCSM) or other disc-associated diseases.

The term "biocompatible" as used in this application refers to a material that is substantially non-toxic in the in vivo environment of its intended use, and that is not substantially rejected by the recipient's physiological system (i.e., is non-antigenic). This can be gauged by the ability of a material to pass biocompatibility tests that typically measure a material's toxicity, infectivity, pyrogenicity, irritation potential, reactivity, hemolytic activity, carcinogenicity and/or immunogenicity. A biocompatible prosthesis, when introduced into a majority of recipients, will not cause a significantly adverse, long-lived or escalating biological reaction or response, and is distinguished from a mild, transient inflammation which typically accompanies surgery or implantation of foreign objects into a living organism.

The term "cervical arthroplasty" as used in this application refers to an operative procedure of orthopaedic surgery performed for replacing the diseased or degenerated cervical disc with disc prosthesis of the present invention.

The term "burr" (sometimes called "rotary file") as used in this application refers to a small cutter used in die grinders, rotary tools or dentist's drills. To maintain the correct surface speed and cutting conditions the burr may be rotated at the highest speed possible, commensurate with its size and construction. Burrs may be made from a variety of materials, such as tungsten carbide, which allows them to run at high speeds, yet still maintain their cutting edges.

This invention provides new disc prosthesis and a method that uses an artificial disc prosthesis that fits into the cervical spinal column of non-human animals. After the spinal cord is decompressed and the bulging, degenerated disc (and optionally the thickened ligaments) is removed, the prosthetic device is placed in the affected area thus restoring mobility to the spine. The prosthetic device is particularly suitable as an artificial cervical disc for large animals, e.g. large dogs.

Certain features disclosed in U.S. Pat. No. 7,276,082 B2 "Artificial Spinal Discs and Associated Implantation and Revision Methods", which discloses an intervertebral device, are related to the present invention, and its disclosure is herein incorporated by reference.

Referring to FIGS. 1-7, the prosthetic device 10 includes two discs, also referred to as two end plates or two shells, that are joined together to form the prosthetic device. These discs or end plates can be anatomically shaped, to roughly follow the shape of the vertebra that is being replaced. The discs can be made of any biocompatible material. The discs can be made of metal, e.g. cobalt or titanium, or alloys thereof. In one example, the titanium alloy used for the prosthetic device is Titanium 6AL4V ELI.

Preferably, the discs have metal-on-metal bearing surface. Different types of metal can be used. One type of metal that can be used is stainless steel, e.g. corrosion-resistant stainless steel (SS) Nitronic 60 and 304-SS, Mc Master-Carr, Chicago, Ill. Some advantages of stainless steel are its corrosion resistance, ability to be cleaned, and the property of being relatively hard yet machinable material. However, non-metallic biocompatible materials can also be used. Non-metallic biocompatible materials can also be mixed with metallic materials to produce the discs of this invention.

In some embodiments, the discs can be made of different materials. For example, the disc that includes protrusion ("ball") can be made of Nitronic 60, chosen for its resistance to galling, which could occur in the rubbing of the ball in the socket. Nitronic 60 stainless steel is an austenitic alloy, considered to have high galling resistance, high pitting resistance, and high corrosion resistance. Nitronic 60 has an oxidation resistance comparable to stainless steel 309 and far better than stainless steel 304 and 316. In addition, the crevice corrosion and chloride pitting resistance of Nitronic 60 is greater than stainless steel 316. At the same time, the other disc, which includes the socket, can be made of different material, e.g. 304 Stainless Steel. Using two different types of stainless steels lowers the chance for galling, where like materials would stick together under frictional movement.

Figure 2:
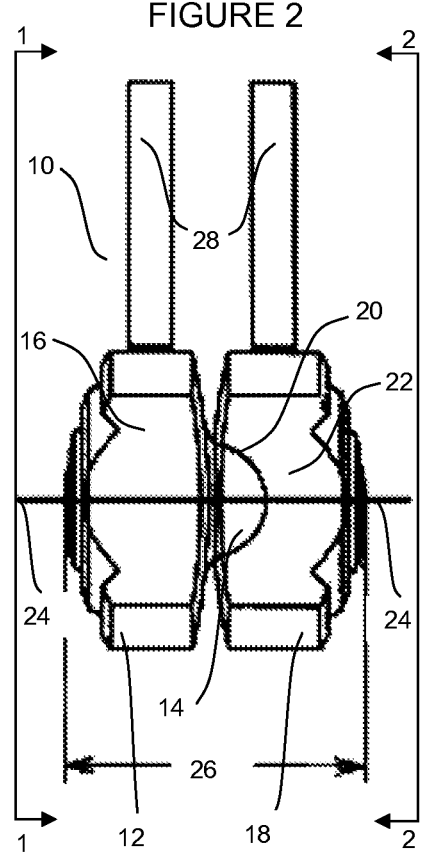
FIG. 2 is a cross-section schematic through the prosthetic device.
Figure 4:
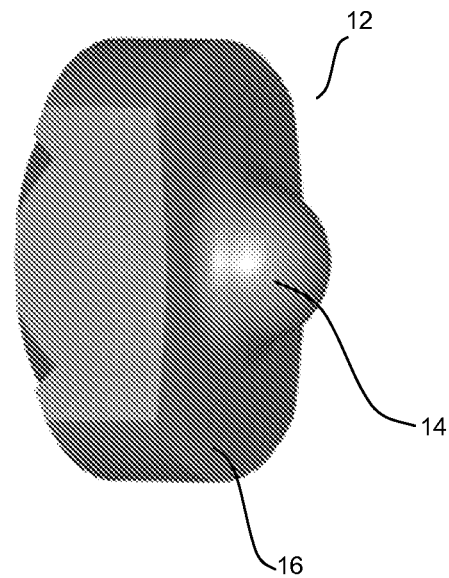
FIG. 4 is a perspective view of one embodiment of a first disc of the prosthetic device comprising a protrusion connected to the disc body.
Figure 5:
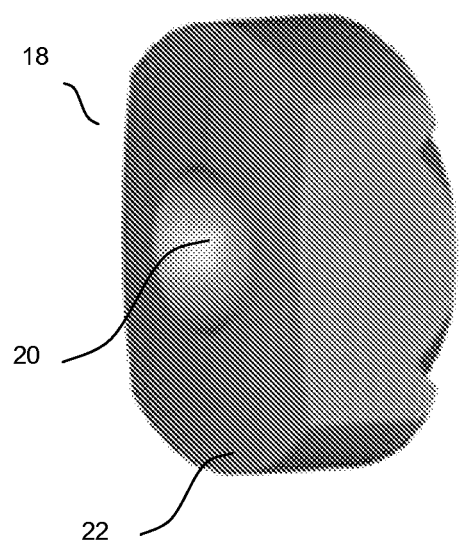
FIG. 5 is a perspective view of one embodiment of a second disc of the prosthetic device comprising a socket recessed in the disc body.
Figure 6:
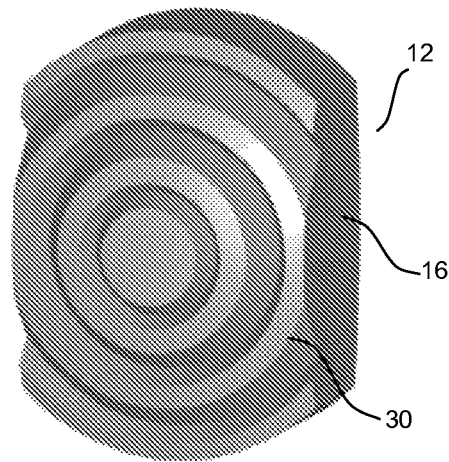
FIG. 6 is a perspective view of one embodiment of a first disc of the prosthetic device.
Figure 7:
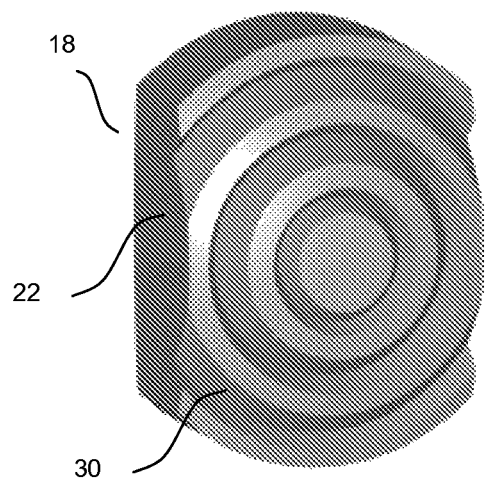
FIG. 7 is a perspective view of one embodiment of a second disc of the prosthetic device.

As shown in FIGS. 2 and 4, the first of the two discs 12 has a protrusion 14 that is connected to the first disc body 16. As shown in FIGS. 2 and 5, the second of the two discs 18 has a socket 20 that is recessed in the second disc body 22. The protrusion 14 may be symmetrically positioned with respect to a central axis of the prosthetic device 24. As well, the socket 20 may be symmetrically positioned with respect to a central axis of the prosthetic device 24.

The prosthetic device 10 is assembled when the first disc 12 is joined to the second disc 18, as shown in FIG. 2. In addition, FIG. 2 illustrates the first disc 12 comprising a protrusion 14 connected to the first disc body 16 and the second disc 18 comprising a socket 20 recessed in the second disc body 22. The protrusion 14 is adapted to fit into the socket 20 to join the first disc 12 with the second disc 18. The protrusion 14 is fit for pivoting movement into the socket 20. The discs are substantially parallel to each other and axially spaced from each other along a central axis 24. The cranial-to-caudal thickness 26 of the assembled prosthetic device is thus dependent on the thickness of the two discs when they are joined together (FIG. 2).

The ball-and-socket configuration of the prosthetic device provides for a range of motion. The range of motion of the prosthetic device may vary. Preferably, the prosthetic device provides a range of motion with approximately thirty degrees of freedom.

In preferable embodiments shown in FIGS. 1-7, side portions of the discs are removed, so that each of the discs has approximately rectangular cross-section. The size of the removed portions can vary. Some examples of the width of the flat (flat side-to-flat side) are shown in Table 1 below. In general, side portions are removed to make the discs more suitable for implantation into a recipient. Because each of the discs that comprise the prosthetic device has approximately rectangular cross-section, when the device is assembled, as shown in FIG. 2, the cross-section of the prosthetic device is approximately rectangular.

The prosthetic device is produced with a size and dimension suitable for implantation into a recipient. The recipient may be a mammal. Preferably, the recipient is a non-human animal recipient, such as a dog. Table 1 provides examples of different sizes of the prosthetic device of the present invention.

TABLE 1

Examples of different sizes of the prosthetic device

| Disc | Assembled width (mm) | Outside diameter (mm) | Width of the flat (mm) | Thickness of the convex disc body (mm) | Thickness of the concave disc body (mm) |
|---|---|---|---|---|---|
| Sm 1 | 9.0 | 10.5 | 7.4 | 6.3 | 4.5 |
| Sm 2 | 10.5 | 10.5 | 7.4 | 7.0 | 5.2 |
| Sm 3 | 12.0 | 10.5 | 7.4 | 7.8 | 5.9 |
| Sm 4 | 14.0 | 10.5 | 7.4 | 7.8 | 5.9 |
| Med 1 | 9.0 | 11.3 | 8.5 | 6.3 | 4.5 |
| Med 2 | 10.7 | 11.3 | 8.5 | 7.1 | 5.4 |
| Med 3 | 12.0 | 11.3 | 8.5 | 7.8 | 5.9 |
| Med 4 | 14.0 | 11.3 | 8.5 | 7.8 | 5.9 |

Figure 3:
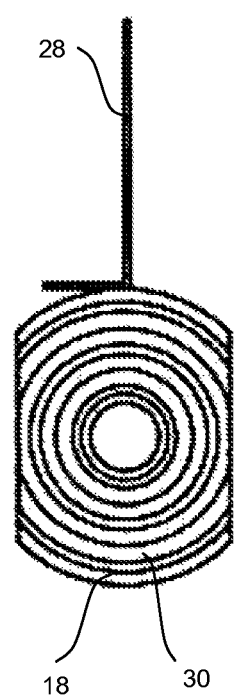
FIG. 3 is a top plan view of a second disc of the prosthetic device taken through line 2-2 in FIG. 2.

Each disc of the prosthetic device may have one or more fins 28. The fins assist with positioning of the prosthetic device during implantation. The fins 28 may be removable. Preferably, the fins are breakable. Upon implantation of the prosthesis in the recipient's body, the fins are removed from the discs, e.g. broken off. The fins 28 can have a variety of shapes. Preferably, the fins 28 are elongated and rectangular, as shown in FIGS. 1-3. The attachment area of the fins to the discs can be perforated for ease of removal.

The fins 28 can be positioned on any part of the disc. Preferably, the fins are positioned on the disc side that corresponds to the dorsal side of the recipient's spinal column. In FIGS. 1-3, the dorsal side corresponds to the top side of the drawings.

Preferably, the implanted prosthesis should maintain stability. This can be achieved by providing a firm contact with, or fixation to, the adjoining vertebrae. To provide stability, the prosthesis includes discs with convex surfaces facing the adjoining vertebrae. These convex surfaces may have topographic features, such as one or more grooves and ridges. This design of the prosthetic device may help bone ingrowth and stabilization of the prosthesis with respect to the adjoining vertebrae. The dimensions of the groves and the ridges may vary. For example, the depth of the groves may be in the range between 0.1 mm and 2.0 mm, and preferably between 0.3 mm and 1.0 mm.

In addition, and if desired, increased stability and/or fixation of the prosthesis may be achieved by one or a combination of the following mechanisms: anchoring through one or several pegs or posts inserted into the vertebrae; physical interfacing via a threaded surface; promotion of bone ingrowth by means of a porous surface; or fixation with screws through a side wing extending from the plate. Any of these methods, or combinations thereof, may be used for practicing the invention.

The back surfaces of each of the two discs, i.e. those surfaces abutting the adjoining vertebrae, have curvature. Preferably, as shown in FIGS. 2 and 4-7, the back surfaces of each disc, abutting the adjoining vertebrae, are convex. Convexity of the surface is desired as it may decrease, prevent, or avoid implant migration. Convexity of the disc surface thus obviates the need for screws or pegs that are typically used to anchor an artificial disc implant.

The outside surfaces of the discs may have topography designed to provide means for bone ingrowth into the discs. Preferably, the disc surfaces abutting the adjoining vertebrae have topographic features. The topography may be designed to promote bone ingrowth at the device-to-vertebral body interfaces. The topography may include grooves and ridges. The size and shape of the topographic features may vary, and they will depend on the size of the discs. The discs may have porous coating, which will also provide for bone ingrowth. While the actual characteristics of the topography are not critical, what is important is that the topography provides an interface for bone ingrowth.

Preferably, and as shown in FIGS. 1-3, 4, and 5, the topographic features include several concentric circles 30. The size and number of concentric circles 30 may vary, and these will depend on the size of the discs and the desired dimensions of the ridges and grooves.

FIG. 1 is a schematic illustrate of a top plan view of the first disc 12 of the prosthetic device 10. The back surface of the first disc is shown. In this example, the first disc is produced with a size and dimension suitable for implantation into a non-human animal recipient. In this example, the back surface has topography in the form of concentric circles 30. The disc has been approximately vertically cut on both the left and the right side, to make it suitable for implantation into the recipient's spinal region. Also shown is a breakable fin 28 that is attached to the dorsal region of the first disc.

FIG. 3 is a schematic illustrate of a top plan view of the second disc 18 of the prosthetic device 10. The back surface of the second disc is shown in FIG. 3. In this example, the back surface has topography in the form of concentric circles 30. The disc has been approximately vertically cut on both the left and the right side, to make it suitable for implantation into the recipient's spinal region. Also shown in FIG. 3 is a breakable fin 28 that is attached to the dorsal region of the second disc.

In principle, the prosthetic device 10 can be used to treat a variety of non-human animals, especially large animals such as horses, bulls, primates, etc. Preferably, the prosthetic device 10 is used to treat dogs, especially relatively large dogs. One advantage of the prosthetic device 10 is that is maintains motion and lessens the chance of domino effect.

The prosthetic device can be produced in a variety of sizes. Preferably, the size of the prosthesis is chosen based on measurements of the cervical dimensions in the recipient subject.

That can be done prior to implantation, e.g., by overlapping implants of different sizes to radiographic images of a cervical spine from the recipient. For example, when the recipient is a dog, implants can be overlapped with X-ray images of the cervical spine from the dog, as shown in FIG. 8. Preferably, the size of the prosthetic device, when used for treatment of large dogs, is in the following ranges: width (lateral-to-lateral) between 6 and 10 mm; height (dorsal-to-ventral) between 9 and 13 mm; thickness (cranial-to-caudal, with the two discs assembled) between 9 and 12 mm.

This invention provides a method for amelioration of debilitating and repetitive spinal injuries in dogs, particularly large dogs. In vertebrates, cervical vertebrae are those vertebrae immediately behind (caudal to) the skull. In many vertebrate species, cervical vertebrae are variable in number; however, almost all mammals have seven cervical vertebrae. These vertebrae are numbered C1-C7. The prosthetic device of this invention can be used for treatment of degenerated or diseased discs along the entire cervical spine. Preferably, the prosthetic device can be used for treatment of a part of the cervical spine, in particular the regions between the vertebra C5-C6 and C6-C7. The majority of disc-related diseases in dogs also occur in these two spinal regions.

The method of providing a prosthetic replacement for a vertebral disc includes removal of the degenerated or diseased disc and then replacement of the removed disc with an artificial disc of this invention. A minimally invasive surgical technique is preferred for practicing the invention.

In one example, an incision is made into the skin on the neck, while the subject is kept in dorsal recumbence. After exposure of the cervical spine and complete removal of the diseased or degenerated disc, the intervertebral space may be restored to its original height with the aid of a spreading system. The remnants of the diseased or degenerated disc and bone outgrowths that press on the nerve roots or the spinal cord can be removed. Finally, the disc prosthesis is inserted and the spreading system is removed. Occasionally, more than one prosthesis may be implanted into the cervical spine. The subject is kept under general anesthesia while the operation is performed.

The prosthetic device of this invention can be introduced into intervertebral space using cervical arthroplasty, which can be performed with modification of the known surgical approaches for treatment of cervical vertebral diseases in the dog, e.g. as described in Koehler et al., 2005, *Am. J. Vet. Res.* 66: 678-687.

Preferably, the surgical procedure performed is a ventral cervical arthroplasty. The surgical incision or approach is made at the front of the neck (anterior) and the diseased or degenerated disc is removed. The empty disc space is filled with the prosthetic device of this invention. Subject's own bone (called autograft) or other graft may be introduced to induce new bone to grow between the vertebrae. A cervical plate and screws may be implanted to provide immediate spinal stability. One example of a procedure that can be used for practicing the present invention is shown in Adamo et al., 2007, *Vet. Surgery* 36: 729-741.

Figure 12:
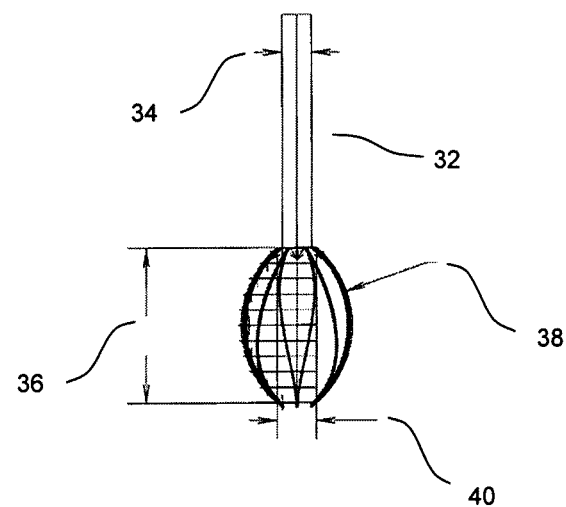
FIG. 12 is a cross-section schematic through one embodiment of a burr used for practicing the present invention.
Figure 13:
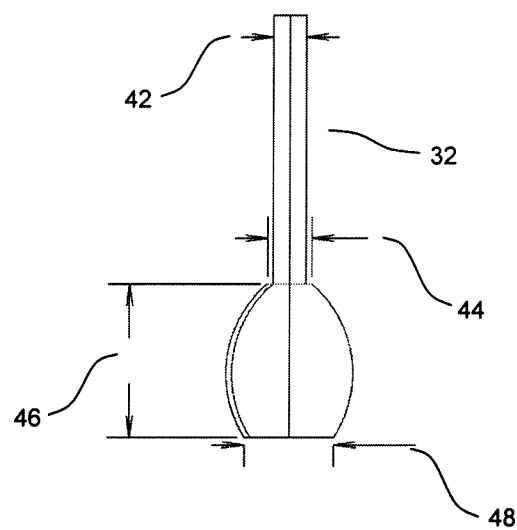
FIG. 13 is a cross-section schematic through another embodiment of a burr used for practicing the present invention.

Cross-section sketches of exemplary burrs 32 useful for practicing the present invention are shown in FIGS. 12 and 13. The shape of the burrs resembles the external convexity of the assembled artificial disc. In the embodiment of a tool (burr) 32 shown in FIG. 12, the dimensions are, e.g., as follows: diameter 34=approximately 2.36 mm; length 36=approximately 12.70 mm; radius 38=approximately 8.36 mm; and diameter 40=approximately 3.17 mm. In the embodiment of a tool (burr) 32 shown in FIG. 13, the dimensions are, e.g., as follows: diameter 42=approximately 2.36 mm; length 44=approximately 3.15 mm; length 46=approximately 10.88 mm; and diameter 48=approximately 6.35 mm. These burrs, as well as burrs with similar dimensions, can be used for milling the vertebral end plate of the ventral slot to better accommodate the implant.

Implantation of the new prosthetic device is expected to decrease the "domino effect" and is expected to improve the prognosis of disc-associated wobbler syndrome in dogs. In disc-associated diseases, the extent of cord compression can vary in flexion, extension and linear traction (distraction). Treatment of the disc-associated disease with the prosthesis of this invention is expected to improve at least one of these parameters.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

A biomechanical study of this prosthesis conducted in the Department of Orthopedics and Rehabilitation, University of Wisconsin-Madison, indicated that canine cervical spines with an implanted prosthesis have biomechanical behaviors more similar to an intact spine compared to the spines treated with other two current surgical techniques.

Study Design.

A canine cervical disc prosthesis was designed. The prosthesis was produced in the Department of Physics Instrument Shop of the University of Wisconsin-Madison. The prosthesis included two stainless steel end plates with metal-on-metal bearing surface, with a range of movement of 30°. The back surface of each end plate was convex to avoid implant migration and had concentric grooves to allow bone ingrowth into the implant. On the dorsal part of the prosthesis two breakable fins were attached to allow handling of the prosthesis during implantation (Adamo et al., 2007).

The prosthesis was made in two different sizes based on cross-sectional cervical spine area measured on MRI of two Dobermans affected by disc-associated CCSM and on two cervical cadaveric specimens of medium sized dogs weighting between 25 and 30 kilograms. In one example, respective sizes of the large and small prostheses were: width (lateral-to-lateral) 8.5 mm and 7.4 mm; height (dorsal-to-ventral) 11.3 mm and 10.5 mm; thickness (cranial-to-caudal, with the two shells assembled) 10.7 mm and 10.5 mm.

Six fresh cadaveric cervical spines having C2 (cervical 2) through T1 (thoracic 1) vertebrae were obtained. The spines were biomechanically tested sequentially in four different conditions: 1) intact specimens; 2) specimens with an artificial disc implanted at C5-C6 intervertebral space; 3) specimens with ventral slot; and 4) specimens with distraction and fixation with smooth pin-poly-methylmethacrylate (pin-PMMA). The kinematic data from the C3-C4, C4-C5, C5-C6 and C6-C7 vertebral motion units (VMUs) were compared among treatments.

Specimen collection and preparation. The cervical spine specimens (C2 trough T1) were collected from mature canine cadavers (25 to 30 kg) that were euthanized for conditions not related to this study. Each spine was harvested with the surrounding musculature and screened with dorsoventral and lateral radiographs to exclude any specimens with gross anatomic abnormality or orthopedic disease. Each spine was then wrapped in a plastic bag and stored at −20° C. The day before the testing, all specimens were moved into a refrigerator at 4° C. to thaw. On the day of testing each specimen was warmed to room temperature, was then kept moist by application of saline (0.9% NaCl) solution, and wrapped in saline solution-moistened towels during preparation and testing procedures.

Before preparation and testing, the bone surfaces of the C2 and T1 vertebral bodies were cleaned, the dens and the cranial edge of C2 and the spinous process of T1 were trimmed to accommodate the specimens in the grips that would attach to the biomechanical testing apparatus. Excessive surrounding paravertebral soft tissue was further dissected leaving the surrounding epaxial spinal musculature (spinalis cervicis mm dorsally, intertrasversarii dorsales and ventrales cervicis laterally, and longus colli ventrally), ligaments and joint capsules intact.

Using a 3.2 mm-diameter drill-bit, two holes were drilled at approximately 90° to each other at the cranial and caudal thirds of both the C2 and T1 vertebral bodies in each specimen. Two 6.35 mm diameter steel rods were placed in each hole. C2 and T1 vertebrae with the rods inserted were fixed in the pots with low melting point polyester resin. A further gentle dissection of the epi-axial musculature from the underlying bone was completed to allow placement of needles for extensometers used to measure relative displacement between vertebrae. After a pre-drilling with a 1.7 mm diameter bit, 18 gauge needles were secured in place dorsally on the mid-portion of the dorsal lamina, ventrally on the vertebral body, and bilaterally on the pedicles of C3, C4, C5, C6 and C7 respectively, and extensometers were attached.

Biomechanical Testing.

Biomechanical testing was conducted on a multi-degree of freedom servo testing system. This system loaded the cervical spines with axial, torsional, and pure bending (i.e., rotational) deformations applied at the grips at C1 and T1 (Kunz et al., 1994, *J. Biomech. Eng.* 116: 371-373). The apparatus used servomotor load actuators for bending loads connected to the axial and torsional actuator in a MTS 858 Bionix testing system. Spinal deformations between adjacent vertebrae were measured with extensometers and used to calculate segmental relative motion at C3-C4, C4-C5, C5-C6, and C6-C7 during application of axial compression, torsion, flexion-extension, and lateral bending. Each specimen was tested sequentially in the intact spine, after the insertion of the artificial disc, in the ventral slot condition, and after fixation with pin-PMMA at C6-C7 intervertebral space, respectively.

Cervical Arthroplasty.

Using an 11 scalpel blade, a fenestration was created across the C5-C6 intervertebral space. The space was then distracted using a self retaining Gasper retractor. With a high-speed drill and a 5×5-mm spherical burr a ventral slot was created preserving the caudal edge of C5 as much as possible. The slot was extended in the cranial and caudal direction by removing the mid-portion of both endplates of C5 and C6 to the cancellous bone. The slot width did not exceed 8.5 mm, the length extended no more than a third of the length of the C6 vertebral body, and followed the oblique angle of the intervertebral space. The slot was extended to the depth of the dorsal longitudinal ligament, which was also removed to allow visual inspection of the spinal canal. Additional cancellous bone was removed as needed from both ends of the slot to fit the convexity of the external surface of the prosthesis.

Figure 8A:
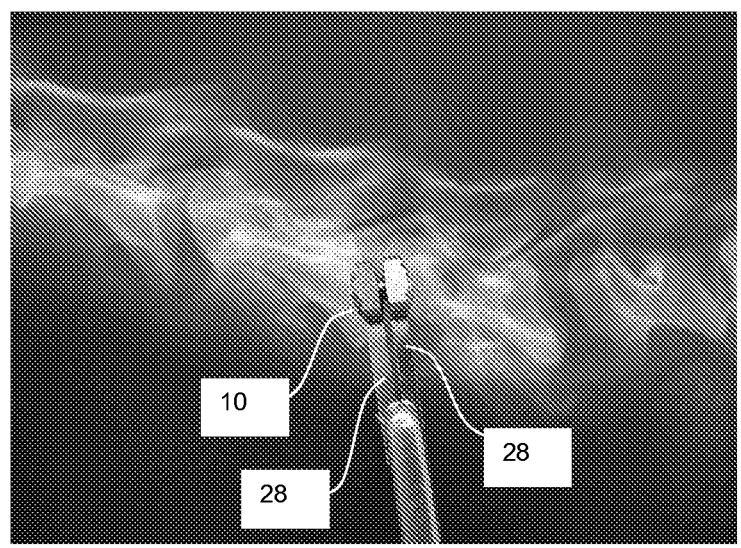
FIG. 8 shows images illustrating the choice of prosthesis size (A, B) and an implanted prosthesis (C).
Figure 8B:
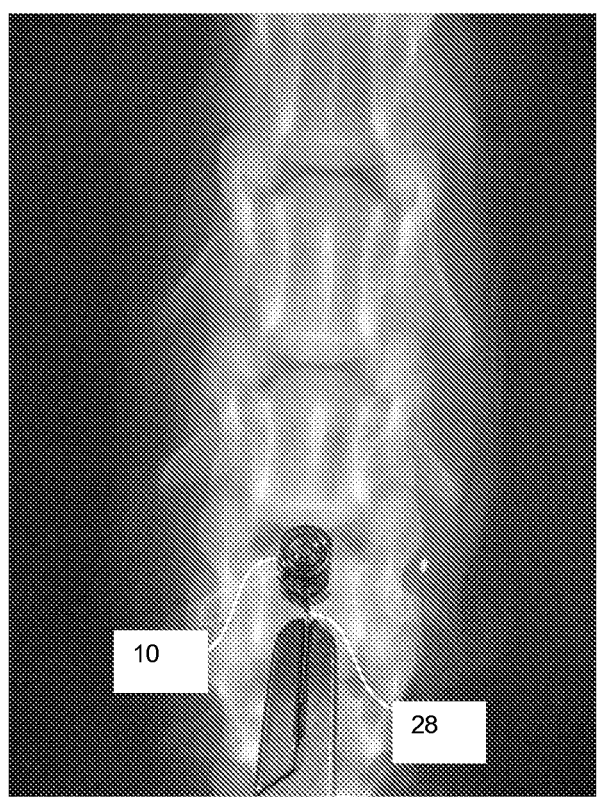
Figure 8C:
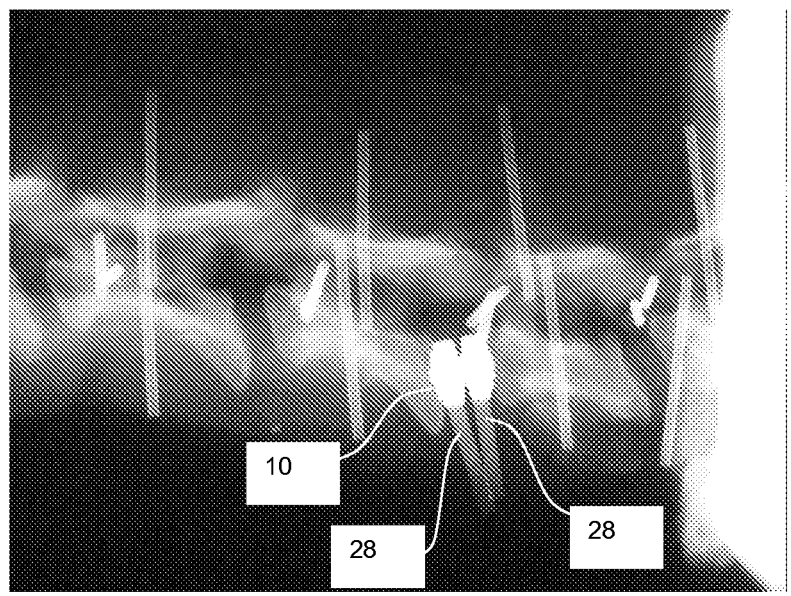

As shown in FIG. 8, the optimal size of a prosthesis 10 that would have the best fit in the intervertebral space was chosen based on overlapping the implant to the lateral (FIG. 8A) and ventro-dorsal (FIG. 8B) radiographic projections of the cervical specimen. In these images, the two parts of the prosthesis are shown as held together using a large needle holder. FIG. 8C is an image of a radiograph showing the implanted prosthesis. In FIG. 8C, images of needles in the vertebrae used to attach the extensometers and fins 28 still attached to the implanted prosthesis 10 are also visible. During implantation the two shells (discs) of the prosthesis were held together by their dorsal fins using a large needle holder which was also used to force (via gentle manual pressure) the prosthesis into the slot while holding the disc before final implantation.

Pin-PMMA Distraction-Fixation Procedure.

Two 3.175-mm-diameter pins were placed trough the vertebral bodies cranial and caudal to the slot at an approximately 30° angle from the sagittal plane in a transverse plane. All pins were inserted to a depth at which the tip of the pin was visibly protruding from the dorsal lamina and they were cut at approximately 5 cm from the point of insertion. A preformed paper mole was placed around the pins to create an oval area to hold the PMMA plug. Specimens were linearly distracted axially with a small tensile force manually applied onto the grips holding the two extremity of the specimen. The polyester resin was mixed at room temperature, poured in the mold and allowed to flow around the pins while the specimen was held in place for a minimum of 20 minutes.

Mechanical Testing Protocol.

Four testing modes were performed: axial compression, torsion, flexion and extension, and lateral bending moments were applied to specimens in the four specimen conditions. Signals from the force transducers and extensometers were collected with a dedicated analog-to-digital data acquisition system sampling at 50 Hz.

In axial compression test, spines were subjected to a 0 to 50 N haversine compressive force that was applied at 0.5 Hz, while other degrees of freedom remained unconstrained and while rigid body motion was measured between vertebrae with extensometers. During torsion, flexion-extension and lateral bending, a static 50 N preload was applied in axial compression and maintained throughout testing. Then a sinusoidal (0.5 Hz) moment with amplitudes of ±1 Nm was applied to the spines. Throughout these tests, other degrees of freedom were unconstrained and the relative displacements and rotations between vertebrae were computed from extensometer and rotational extensometer data.

The data were processed using custom-designed software routines and collected in a spreadsheet file for later statistical analysis. Specimens were removed and subsequently reinserted in test fixtures between treatments. Data for the C3-C4, C4-C5, C5-C6, and C6-C7 VMUs were compared among treatments. After testing the specimens in the four different conditions, radiographs of the specimens were repeated to assess pins placement and to evaluate potential vertebral fracture.

Statistical Analysis.

The mean+/−standard deviation (SD) for all data were calculated. A one way analysis of variance (ANOVA) was used to evaluate the effect of cervical level on the mechanical properties of each tested group and repeated measures ANOVA was used to determine the effect of group at each cervical level. When ANOVA revealed significant differences, a Duncan's Multiple Range Test was performed to separate these differences. Differences were considered to be significant at a probability level of 95% ($p<0.05$). All statistical analyses were performed with a commercially available software program SAS Version 8e, SAS Institute Inc., Cary, N.C.

Results.

Figure 9:
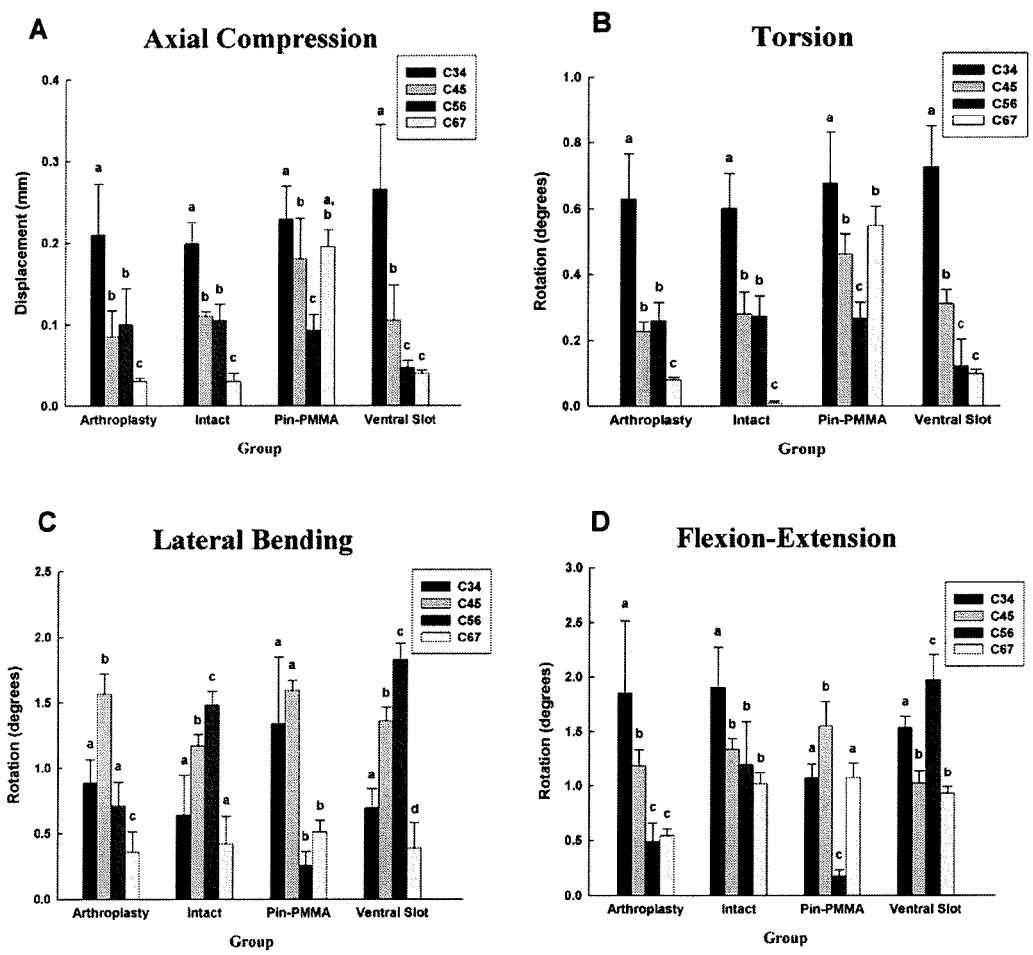
FIG. 9 shows graphs illustrating the effect of cervical level on the mechanical properties of each tested group.
Figure 10:
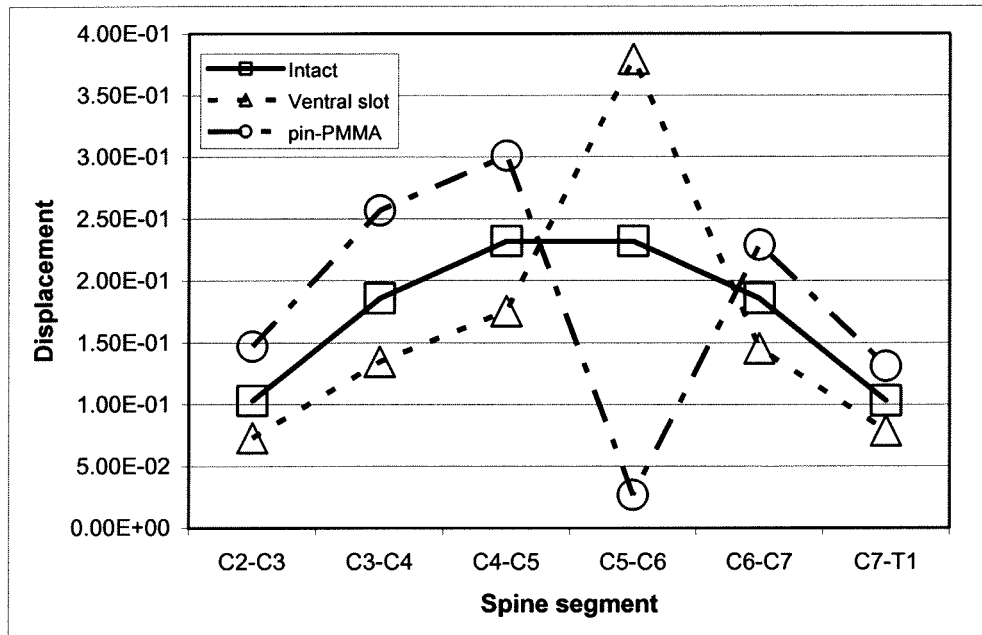
FIG. 10 is a graph illustrating the numerically evaluated gap displacement of three spine configurations for the top-free and bottom-free models.
Figure 11:
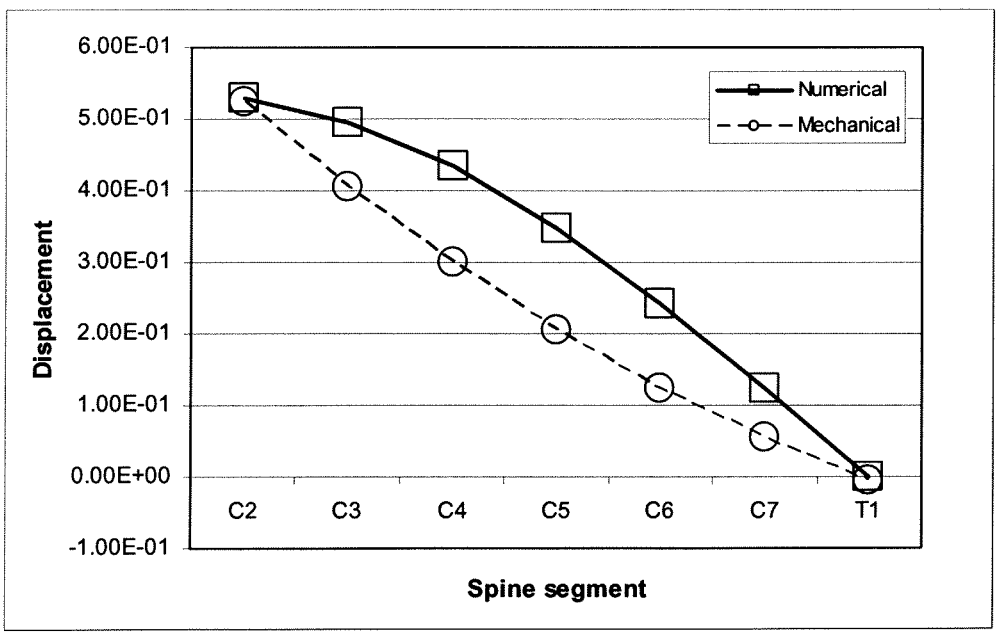
FIG. 11 is a graph illustrating the predicted displacement distribution for axial compression and torsion motion for both numerical simulation and mechanical testing.

This biomechanical study analyzed the effect of disc arthroplasty on cervical spine in a canine cadaveric model. The study assessed the ability of a canine disc arthroplasty to restore the intact cervical kinematics of dogs, comparing surgery for disc-associated CCSM to ventral slot and to pin-PMMA distraction-fixation procedures. The C5-C6 intervertebral space was used as a model and the implant application was able to induce cervical spine kinematics more similar to the intact spines when compared to the ventral slot and pin-PMMA test groups. Each mode of loading is discussed separately with accompanying figures showing the peak displacements or rotations for the 50 N load or the 1 Nm moment. FIG. 9 shows the effect of cervical level on the mechanical properties of each tested group. The cervical levels shown for each tested group are presented with bars C3C4 (corresponding to C3-C4 VMU), C4-C5 (corresponding to C4-C5 VMU), C5-C6 (corresponding to C5-C6 VMU), and C6-C7 (corresponding to C6-C7 VMU). Differences were considered significant at a probability level of 95% ($p<0.05$). The letters over the data bars (a, b, c, d) in FIG. 9 indicate the presence or absence of statistical significance when comparing the biomechanical features between treatments at each segment during each biomechanical testing. NS means non-statistical significance.

Axial Compression.

The intersegmental kinematic responses to a 50 N compressive load are shown in FIG. 9A. Overall, displacements were larger cranially and smaller caudally in all groups except for the pin-PMMA group, which had similar displacement at C6-C7 VMU compared to C3-C4 and C4-C5. After implantation of the artificial disc of this invention, the VMUs were similar to the intact spine at all 4 levels. C5-C6 VMUs with a ventral slot showed higher inter-segmental stiffness (lower motion) than the other treatments. Pin-PMMA fixation specimens at C5-C6 VMU were similar to intact specimens and arthroplasty specimens in displacement, although larger displacements were induced in the adjacent VMUs. At the treated VMU, except for the ventral slot, there was no statistically significant difference between arthroplasty, intact, and pin-PMMA groups.

Torsion.

The intersegmental kinematic responses to the torsional loading are shown in FIG. 9B. The pattern is similar to axial compression with inter-segmental rotations larger cranially and smaller caudally except for the pin-PMMA group. After implantation of the artificial disc of this invention, the VMUs were similar to the intact spine, except at C6-C7 which exhibited more motion than the intact group. The C5-C6 VMUs with a ventral slot showed a higher inter-segmental stiffness than the other treatments. Pin-PMMA fixation specimens at C5-C6 VMU were similar to intact and arthroplasty specimens in displacement, although larger displacements were induced in the adjacent VMUs. At C5-C6 VMU, results were similar to axial compression, and except for the ventral slot, there was no statistically significant difference between arthroplasty, intact, and pin-PMMA groups. At the adjacent VMU C4-C5, only the arthroplasty group had similar motion to the intact group. At the adjacent VMU C6-C7, there was significant statistical difference between all treated groups and the intact specimens. No significant statistical difference was observed at C3-C4 VMU between all groups.

Lateral Bending.

The intersegmental kinematic responses to lateral bending are shown in FIG. 9C. The motion in spines with a ventral slot was similar to intact spines except for increased motion at C4-C5 and C5-C6 VMUs. Pin-PMMA fixation showed an abrupt change between the fixed C5-C6 VMU and adjacent VMUs with increased rigidity of C5-C6 compared to intact specimen and the other treatments. At the treated VMU, there was a statistically significant difference between all groups with the intact group demonstrating more motion than the arthroplasty and pin-PMMA groups, and less motion than the ventral slot group. At the adjacent C4-C5 VMU, there was also a statistically significant difference between all treated groups and the intact specimens, while at the adjacent C6-C7 VMU there was no significant statistical difference between the 4 groups. At C3-C4 VMU, except for pin-PMMA, there was no statistically significant difference between arthroplasty, intact, and ventral slot groups.

Flexion-Extension.

The intersegmental kinematic responses to flexion and extension (flexion-extension) are shown in FIG. 9D. The spines with a ventral slot had increased motion at C5-C6 VMU compared to intact spines and the two treatment groups. Spines with pin-PMMA fixation showed more rigidity than other treatments at the fixed C5-C6 VMU, with abrupt changes at adjacent VMUs when compared to other treatments. At the treated VMU, there was a statistically significant difference in motion among all treated groups and the intact specimens. At the adjacent VMU C4-C5, arthroplasty was the only treatment with no statistically significant difference compared to the intact group, while at the adjacent C6-C7 VMU arthroplasty was the only treatment with statistically significant different motion compared to the intact specimens. At VMU C3-C4, pin-PMMA fixation had statistically significant less motion than the intact group and the other two experimental groups.

Ventral Slot.

The slots were created to fit the size of the prosthesis and they did not exceed in size the clinical recommendation that slot length should not extend beyond the caudal third of the cranial vertebra or beyond the cranial third of the caudal vertebra, and that slot width should not exceed one third to three fourths of the vertebral body. Clinically, the ventral slot procedure has been associated with vertebral subluxation when the ratio between slot width and vertebral body width is greater than 0.5. Following these anatomic recommendations laceration of the ventral vertebral sinus and basivertebral veins and vertebral subluxation is minimized.

Creation of ventral slot showed significant changes in all the modalities tested at the treated site, thus likely enhancing vertebral instability at this level. The ventral slot technique may also reduce the energy required to collapse the intervertebral disc place, which could also predispose to foraminal compression and bulging of the residual dorsal annulus fibrosus in the ventral canal. However, this mechanical instability could in vivo be compensated and neutralized by the muscular subsystems. It is also likely that the degree of the vertebral instability induced at the treated site at the time of surgery may decrease during the following months due to secondary fibrosis.

The changes associated with the creation of the ventral slot affect the mechanism of adjacent VMUs. After creation of the ventral slot at the C5-C6 intervertebral space, there was a concomitant increase in rotation at the adjacent C6-C7 VMU, an increased degree in lateral bending, and a decreased degree in flexion-extension at the adjacent cranial VMU.

When the intersegmental biomechanical characteristics between ventral slot and intact spines groups were compared, both ventral slot and intact spines revealed statistically significant increasing motion from C3-C4 to C4-C5 and C5-C6, which then decreased at C6-C7. The significant changes in the intersegmental biomechanical compared to the intact spine observed in all other modes of testing may be one of the factors responsible for the domino lesions.

Pin-PMMA.

Pin-PMMA fixation resulted in a large reduction in rotation at the treated site in lateral bending and flexion-extension, while the displacement in axial compression and the rotation in torsion were similar to the intact spines. The resulting reduction of excessive cervical extension at the treated site may prevent exacerbation of bulging of the dorsal annulus fibrosus and dorsal longitudinal ligament in the spinal canal.

Pin-PMMA fixation affected the biomechanics of adjacent VMUs and a larger displacement in axial compression and increased rotation in torsion were induced at both adjacent VMUs. This was particularly evident at the adjacent VMU caudal to the treated site. In lateral bending and torsion, increased motion was also induced at the adjacent VMU cranial to the treated site. These changes at the sites adjacent to the treated site may be the result of compensation for the reduction in mobility at the treated site. This overloading at the adjacent VMUs could predispose to disc degeneration and domino lesion.

Significantly increased motion in axial compression and torsion compared to the intact spines were particularly evident at the caudal adjacent VMU. Significant differences in the intersegmental biomechanics were also observed in lateral bending and flexion-extension. These may occur due to the significant decrease in degree of motion at the treated site. These significant changes in the intersegmental biomechanics compared to the intact spine may be, as in the ventral slot group, one of the factors responsible for the domino lesion.

Arthroplasty.

Arthroplasty resulted in similar displacement in axial compression and torsion compared to intact spines. However, decrease in rotation was seen in lateral bending and flexion-extension, in comparison to the intact spines. The decrease of rotation at the treated site did not affect the adjacent cranial VMU in axial compression and torsion but it was likely responsible for the increased rotation observed in lateral bending at this site. Decreased rotation was observed at the adjacent caudal VMU in torsion, while increased rotation was observed in flexion-extension at this site. The changes observed at the adjacent VMU could be secondary to the decreased rotation at the treated site, which may be a function of the degree of freedom of the prosthesis or the result of a not-perfect fit of the implant. This could be further evaluated and potentially improved by increasing the degree of freedom of the artificial disc.

In the intersegmental biomechanics characteristic, no significant differences between the prosthesis and the intact spines were observed in axial compression and torsion. However, significant differences were observed in lateral bending and flexion-extension. This could occur due to the decreased degree of rotation allowed by the prosthesis at the treated site or by the not-perfect fit of the implant.

Overall, the artificial disc of the present invention was better able to mimic the behavior of the intact spines compared to the ventral slot and pin-PMMA groups, producing virtually the same displacements and rotations as the intact spines in axial compression and torsion, respectively, but limiting somewhat rotations in flexion-extension and in lateral bending. An artificial prosthesis with an increased degree of freedom at the treated site could potentially overcome some of the dissimilarities observed between the prosthesis used in this study and the intact spines. Simulation of fusion with pin-PMMA significantly reduced motion at the surgical site, which was compensated for by increased motion at the adjacent VMUs. This increased motion at the adjacent VMUs may accelerate degeneration of adjacent intervertebral discs. Restoring a cervical spine biomechanics as close as possible to that of the intact spine may reduce the risk of the domino effect.

The implantation of cervical disc prosthesis after ventral slot in diseased animals, particularly dogs with disc-associated CCSM, has the potential to achieve the goals of spinal decompression, restoration of the biomechanics at the surgical treated sites, and sparing adjacent VMUs from the alterations in loading associated with existing surgical procedures. An additional advantage of cervical arthroplasty over pin-PMMA fixation is the lack of potential complication associated with pin impingement on neurovascular structures, which may be responsible for pain and recurrence of neurologic dysfunctions similar to a domino lesion. Use of cervical arthroplasty to treat disc-associated CCSM may minimize or alleviate the adjacent domino effect.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in clinical prevention and therapy, obvious to those skilled in the art, are within the scope of this invention. All publications, patents, and patent applications cited herein are incorporated by reference in their entirety for all purposes.

What is claimed is:

1. A cervical disc prosthesis for nonhuman large mammals comprising:
   a first disc comprising:
      a first disc body with top and bottom surfaces,
      wherein the top surface has a protrusion, the protrusion being unitary with the top surface, and
      wherein the bottom surface is convex and comprises one or more concentric circles for bone ingrowth into the first disc;
   a second disc comprising:
      a second disc body with top and bottom surfaces,
      wherein the bottom surface is convex and comprises one or more concentric circles for bone ingrowth into the second disc, and
      wherein the top surface has a socket recessed therein;
   wherein the first disc and the second discs are made from stainless steel, wherein the type of stainless steel of the first disc differs from the type of stainless steel of the second disc;
   at least one removable fin attached to a side surface of at least one of the discs;
   wherein the removable fin extends along with two non-parallel axes;
   wherein the protrusion of the first disc is sized and shaped to pivot in the socket of the second disc;
   wherein the first and second discs remain substantially parallel to and axially spaced from each other with their top surfaces facing each other;
   wherein the first disk coaptates with the second disk to provide pivoting movement, the movement having a range of motion with approximately thirty degrees of freedom; and
   wherein, when the cervical disc prosthesis is implanted between adjacent vertebrae, the first and the second discs remain operably connected to each other without a locking mechanism.

2. The prosthesis of claim 1, wherein the protrusion is arranged symmetrically on the first disc.

3. The prosthesis of claim 1, wherein the socket is arranged symmetrically on the second disc.

4. The prosthesis of claim 1, whose cross-section is approximately rectangular.

5. The prosthesis of claim 1, wherein the first disc is a caudal disc and the second disc is a cranial disc.

6. The prosthesis of claim 1, wherein the first disc is a cranial disc and the second disc is a caudal disc.

7. The prosthesis of claim 1, wherein at least one disc is made of stainless steel.

8. The prosthesis of claim 1, wherein at least one disc is made of titanium alloy.

9. The prosthesis of claim 1 wherein the at least one removable fin assists with positioning of the prosthesis during implantation, wherein the at least one removable fin is removed from the discs after implantation.

10. The prosthesis of claim 1, which is sized to fit between two cervical vertebrae in a dog.

11. A method for implanting cervical disc prosthesis for nonhuman large mammals into an intervertebral disc area defined between adjacent cervical vertebrae comprising introducing into the intervertebral disc area the cervical disc prosthesis of claim 1.

12. The method of claim 11, wherein introducing is performed using cervical arthroplasty.

13. Intervertebral disc prosthesis for nonhuman large mammals for placement between two adjacent cervical vertebrae, comprising:
- a first end member for contacting the first vertebra when implanted, the first end member comprising a top concave surface and comprising a bottom convex surface facing the first vertebra, wherein the bottom convex surface comprises one or more concentric circles for bone ingrowth into the first end member, wherein the first end member has a central axis and wherein the concave surface has a central axis,
- a second end member for contacting the second vertebra when implanted, the second end member being unitary and comprising a top convex surface facing the first end member and comprising a bottom convex surface facing the second vertebra, wherein the bottom convex surface comprises one or more concentric circles for bone ingrowth into the second end member, wherein the second end member has a central axis and the top convex surface has a central axis, at least one convex surface facing at least one cervical vertebra comprises a concentric groove,
- wherein the first disc and the second discs are made from stainless steel, wherein the type of stainless steel of the first disc differs from the type of stainless steel of the second disc, and
- at least one removable fin attached to a side surface of at least one of the end members;
- wherein the removable fin extends along with two non-parallel axes;
- wherein the second end member remains substantially parallel to the first end member and axially spaced from the first end member, and
- wherein the top concave surface of the first end member coaptates with the top convex surface of the second end member to provide pivoting movement, the movement having a range of motion with approximately thirty degrees of freedom, and
- wherein when the intervertebral disc prosthesis is implanted between adjacent vertebrae, the first and second end members remain operably connected to each other without a locking mechanism.

14. The prosthesis of claim 13, wherein the axes are coaxial.

15. The prosthesis of claim 13, whose cross-section is approximately rectangular.

16. The prosthesis of claim 13, wherein at least one disc is made of stainless steel.

17. The prosthesis of claim 13, wherein at least one disc is made of titanium alloy.

18. The prosthesis of claim 13, wherein at least one removable fin assists with positioning of the prosthesis during implantation, wherein the at least one removable fin is removed from the discs after implantation.

19. The prosthesis of claim 13, which is sized to fit between two cervical vertebrae in a dog.

20. A method for implanting intervertebral disc prosthesis for nonhuman large mammals into an intervertebral disc area defined between adjacent cervical vertebrae comprising introducing into the intervertebral disc area the intervertebral disc prosthesis of claim 13.

21. The method of claim 20, wherein introducing is performed using cervical arthroplasty.

* * * * *